United States Patent [19]

Lee et al.

[11] Patent Number: 4,885,389

[45] Date of Patent: Dec. 5, 1989

[54] PROCESS FOR MANUFACTURING P-AMINOPHENOL

[75] Inventors: Lain-tze Lee; Mei H. Chen; Chung-Niang Yao, all of Hsin, Taiwan

[73] Assignee: Industrial Technology Research Institute, Taiwan

[21] Appl. No.: 59,738

[22] Filed: Jun. 8, 1987

[51] Int. Cl.$^4$ .............................................. C07C 85/11
[52] U.S. Cl. ................................................... 564/418
[58] Field of Search .......................................... 564/418

[56] References Cited

U.S. PATENT DOCUMENTS

| 2,525,515 | 10/1950 | Bean | 260/575 |
| 3,383,416 | 5/1968 | Benner | 260/575 |
| 3,654,365 | 4/1972 | Daunis et al. | 260/575 |
| 4,625,062 | 11/1986 | Nagata et al. | 564/416 |
| 4,723,030 | 2/1988 | Davis | 560/19 |

Primary Examiner—Richard L. Raymond
Assistant Examiner—Peter G. O'Sullivan
Attorney, Agent, or Firm—Darby & Darby

[57] ABSTRACT

A process for the reduction of nitrobenzene is described. The reaction is performed catalytically in an aqueous acid medium in the presence of a small amount of organic acid, such as a lower carboxylic acid, oxalic acid, methanesulfonic acid or trichloroacetic acid.

19 Claims, No Drawings

PROCESS FOR MANUFACTURING P-AMINOPHENOL

BACKGROUND OF THE INVENTION

This invention relates to an improved process for the preparation of p-aminophenol by the catalytic hydrogenation of nitrobenzene. p-Aminophenol is a well-known and very useful industrial chemical. It is used as an intermediate in the production of pharmaceuticals such as acetaminophen, in the production of dyestuffs such as sulfur dyes, and in making photographic chemicals.

There are many well-known methods for the production of p-aminophenol. The main processes involve the reduction of nitrophenol or the reduction of nitrobenzene in dilute sulfuric acid over platinum catalyst as shown by the following reactions:

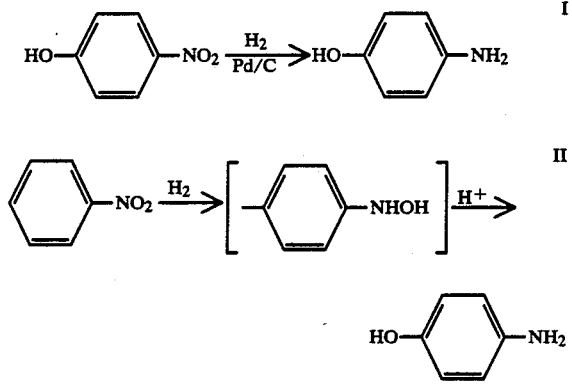

Reaction I suffers from the disadvantage of higher raw material cost, while Reaction II is sensitive to changes in reaction conditions, e.g., temperature, hydrogen pressure, mode of addition and acid concentration, which significantly influence both the yield and quality of p-aminophenol isolated.

In the prior art, U.S. Pat. No. 2,198,249 (Du Pont) discloses the use of high temperatures, e.g., 135°–155° C., and concentrated sulfuric acid for the production of p-aminophenol. The hydrogen pressure is from about 400 to about 500 psi. The yields of the product, however, are relatively low and the final product of poor purity.

In U.S. Pat. No. 2,765,342 (Du Pont), nitrobenzene is reduced catalytically to p-aminophenol under a partial pressure of hydrogen of less than 760 mm Hg with the careful addition of nitrobenzene to the reaction mixture so that the unreacted nitrobenzene does not exceed its solubility in the reaction mixture.

U.S. Pat. No. 3,383,416 (Benner) shows the problem of recovery of the expensive platinum catalyst from the hydrogenation of nitrobenzene to obtain p-aminophenol. This is accomplished by terminating the reaction when about 85–95% nitrobenzene has reacted.

Other processes, such as disclosed in U.S. Pat. No. 3,535,382 (CPC International), show the use of a surfactant or a phase transfer catalyst to facilitate the solubilization of the nitrobenzene to avoid the necessity of adding the reactants in stages.

In all of the aforesaid methods, the p-aminophenol obtained as the end product is relatively impure and the operation is difficult, especially in large scale production.

BRIEF DESCRIPTION OF THE INVENTION

As a general matter, nitrobenzene, when reduced first to form phenylhydroxylamine, can be further reduced to form aniline. In the presence of acid, phenylhydroxylamine undergoes the rearrangement shown in Reaction III. As will be noted, after the formation of phenylhydroxylamine, there are two competitive reaction pathways leading to the final products, aniline and p-aminophenol.

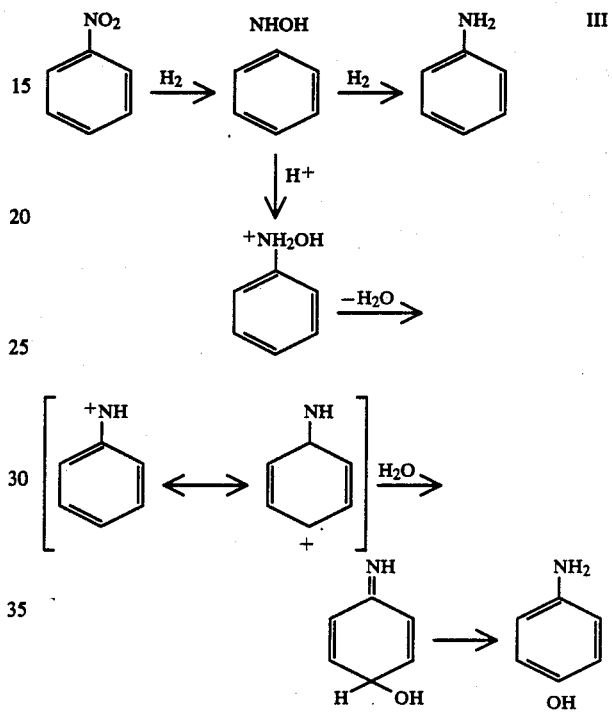

In accordance with the invention, it has now been discovered that the selectivity to p-aminophenol can be substantially improved by carrying out the catalytic hydrogenation reaction in an acidic aqueous reaction medium in the presence of an organic acid. It is believed that this process stabilizes the phenylhydroxylamine by forming an ion pair with the organic acid and the partitioning of the intermediate into the aqueous solution.

DETAILED DESCRIPTION OF THE INVENTION

The hydrogenation of the nitrobenzene to p-aminophenol is carried out in an acid aqueous medium, most preferably in a solution of sulfuric acid. Generally, the sulfuric acid concentration is in the range of from 2.5% to 30%, most preferably from 10 to 25%. Acids other than sulfuric, such as phosphoric and hydrochloric, may be used; however, lower rates and yields of the desired p-aminophenol are obtained.

The temperature of the reaction may be from 40° to 120° C., preferably from 60° to 100° C. Sufficient pressure is maintained to insure that the reaction medium remains in the liquid phase; generally speaking, a reaction pressure of from 20 psi to 80 psi, preferably from 40 psi to 60 psi, is used.

Suitable catalysts are the noble metals, preferably platinum and palladium, supported on charcoal or alumina. From 1% to 5% of the catalyst on the support should be used. Based on the reaction medium, from $8.5 \times 10^{-5}$ to $6.8 \times 10^{-4}$, based on the metal, should be used for each 100 parts of the reaction medium.

The hydrogenation is performed by passing hydrogen into a sealed reaction zone at a partial pressure of from 20 psi to 80 psi, preferably from 40 psi to 60 psi. The reaction is carried on to completion, as is evidenced by the discontinuance of hydrogen uptake. The reaction period may range from 1 to 10 hours; generally from 2 to 6 hours is sufficient.

A wide range of organic acids may be used in order to obtain the benefit of the instant invention. Generally from 0.1 to 1%, based on the weight of the aqueous medium, is employed. Preferably from 0.4 to 0.8% is used. Higher amounts may be used, but these do not offer any advantage. Preferred organic acids are the lower carboxylic acids having from 1 to 4 carbon atoms, halogenated carboxylic acids, and sulfonic acids. Examples of these materials include formic acid, acetic acid, propionic acid, trichloroacetic acid and methanesulfonic acid.

Optimum conditions of temperature, pressure and catalyst concentration may be readily determined by those skilled in the art. As a general matter, increasing these operating conditions increases the conversion of the nitrobenzene but, if raised excessively, may decrease the ratio of the p-aminophenol obtained with respect to the aniline produced.

In order to illustrate the invention more clearly, attention is directed to the following example:

A 200 ml Parr shaker was charged with 12.3 g of nitrobenzene, 0.015 g of 3% platinum on charcoal catalyst and 120 g of 15% sulfuric acid, and the organic acid (if any) indicated in the following table. After the charged vessel was sealed and purged with hydrogen, it was heated and maintained at a temperature of 80° C. under a pressure of 4.2 kg/cm² pressure of hydrogen. Hydrogenation was completed in the time indicated in the Table, the catalyst filtered off, and the aniline and p-aminophenol determined:

TABLE

| Organic Acid, | grams | Reaction time, hours | p-Aminophenol grams | % of theory | Aniline grams | % of theory |
|---|---|---|---|---|---|---|
| None | — | 5 | 7.39 | 67.8 | 1.73 | 18.6 |
| Methanesulfonic acid | 0.5 | 3 | 7.69 | 70.5 | 1.60 | 17.2 |
| Acetic acid | 0.5 | 3 | 8.15 | 74.8 | 1.7 | 18.3 |
| Formic acid | 1.0 | 3.5 | 8.66 | 79.5 | 1.56 | 16.8 |
| Formic acid | 0.5 | 2.5 | 9.08 | 83.3 | 1.52 | 16.3 |
| Formic acid | 0.1 | 4 | 8.4 | 77.1 | 1.75 | 18.8 |
| Oxalic acid | 0.5 | 4 | 8.4 | 77.1 | 1.7 | 18.2 |
| Trichloroacetic acid | 0.5 | 4 | 8.63 | 79.2 | 1.54 | 16.6 |

The above data clearly show that the addition of a wide variety of organic acids improves the yield and selectivity to the p-aminophenol. This unobvious result is of significant commercial importance.

What is claimed is:

1. A process for preparing p-aminophenol which comprises: catalytically hydrogenating nitrobenzene in an acidic aqueous reaction medium containing from 10 to 25% sulfuric acid in the presence of from 0.1 to 1%, based on the weight of aqueous medium, of an organic acid.

2. The process of claim 1 wherein said organic acid is carboxylic acid containing from 1 to 4 carbon atoms.

3. The process of claim 1 wherein the organic acid is a sulfonic acid.

4. The process of claim 1 wherein the organic acid is methanesulfonic acid.

5. The process of claim 2 wherein the organic acid is acetic acid.

6. The process of claim 2 wherein the organic acid is formic acid.

7. The process of claim 1 wherein the organic acid is oxalic acid.

8. The process of claim 1 wherein the organic acid is trichloroacetic acid.

9. The process of claim 1 wherein the hydrogenation catalyst is a supported platinum or palladium catalyst.

10. The process of claim 9 wherein the catalyst is supported on carbon.

11. The process of claim 1 wherein the hydrogenation is performed at a temperature of from 60° to 100° C.

12. A process for preparing p-aminophenol which comprises: catalytically hydrogenating nitrobenzene in the presence of a platinum on carbon supported catalyst at a temperature of from 60° to 100° C. in an acidic aqueous reaction having from 10 to 25% sulfuric acid and additionally medium containing from 0.1 to 1%, based on the weight of the aqueous medium, of an organic acid.

13. The process of claim 12 wherein said organic acid is carboxylic acid containing from 1 to 4 carbon atoms.

14. The process of claim 12 wherein the organic acid is a sulfonic acid.

15. The process of claim 12 wherein the organic acid is methanesulfonic acid.

16. The process of claim 13 wherein the organic acid is acetic acid.

17. The process of claim 13 wherein the organic acid is formic acid.

18. The process of claim 12 wherein the organic acid is oxalic acid.

19. The process of claim 12 wherein the organic acid is trichloroacetic acid.

* * * * *